(12) United States Patent
Birkett et al.

(10) Patent No.: US 8,481,659 B2
(45) Date of Patent: Jul. 9, 2013

(54) CURE ACCELERATORS FOR ANAEROBIC CURABLE COMPOSITIONS

(75) Inventors: David P. Birkett, Kildare (IE); Martin Wyer, Meath (IE); Andrew Messana, Newington, CT (US); Philip Klemarczyk, Canton, CT (US); Anthony F. Jacobine, Meriden, CT (US)

(73) Assignees: Henkel Corporation, Rocky Hill, CT (US); Henkel Ireland Ltd., Monheim (DE)

( * ) Notice: Subject to any disclaimer, the term of this patent is extended or adjusted under 35 U.S.C. 154(b) by 0 days.

(21) Appl. No.: 13/269,138

(22) Filed: Oct. 7, 2011

(65) Prior Publication Data

US 2012/0157641 A1 Jun. 21, 2012

Related U.S. Application Data

(63) Continuation of application No. PCT/US2010/032873, filed on Apr. 29, 2010.

(60) Provisional application No. 60/174,614, filed on May 1, 2009.

(51) Int. Cl.
*C08F 120/68* (2006.01)
*C07D 215/06* (2006.01)

(52) U.S. Cl.
USPC ........ 526/204; 526/320; 526/205; 526/217; 526/227; 526/230; 526/321; 526/165; 526/166

(58) Field of Classification Search
USPC ............. 526/204, 205, 217, 227, 230, 320, 526/321; 546/165, 166
See application file for complete search history.

(56) References Cited

U.S. PATENT DOCUMENTS

| | | | |
|---|---|---|---|
| 3,218,305 A | 11/1965 | Krieble | |
| 3,625,930 A | 12/1971 | Toback et al. | |
| 3,970,505 A | 7/1976 | Hauser et al. | |
| 4,180,640 A | 12/1979 | Melody et al. | |
| 4,259,462 A | 3/1981 | Nakano et al. | |
| 4,287,330 A | 9/1981 | Rich | |
| 4,321,349 A | 3/1982 | Rich | |
| 4,324,349 A | 4/1982 | Kaufman | |
| 4,588,639 A | 5/1986 | Ozono | |
| 4,812,497 A | 3/1989 | Mochizuki | |
| 5,041,508 A | 8/1991 | Haruna et al. | |
| 5,411,988 A | 5/1995 | Bockow et al. | |
| 5,489,622 A | 2/1996 | Hara et al. | |
| 5,605,999 A | 2/1997 | Chu et al. | |
| 5,811,473 A | 9/1998 | Ramos et al. | |
| 6,391,993 B1 | 5/2002 | Attarwala et al. | |
| 6,583,289 B1 | 6/2003 | McArdle et al. | |
| 6,596,808 B1 * | 7/2003 | Newberth et al. | 524/812 |
| 6,835,762 B1 * | 12/2004 | Kelmarczyk et al. | 523/176 |
| 6,852,778 B1 | 2/2005 | Kusuyama | |
| 6,897,277 B1 | 5/2005 | Klemarczyk et al. | |
| 6,958,368 B1 | 10/2005 | Klemarczyk et al. | |
| 7,411,009 B1 * | 8/2008 | Messana et al. | 523/176 |
| 2003/0207126 A1 | 11/2003 | Zhu et al. | |
| 2005/0215655 A1 | 9/2005 | Bilodeau | |
| 2005/0230960 A1 | 10/2005 | Bilodeau et al. | |

FOREIGN PATENT DOCUMENTS

| | | |
|---|---|---|
| DE | 1817989 | 5/1981 |
| DE | 2806701 | 6/1985 |
| FR | 1581361 | 9/1969 |
| JP | 7308757 | 11/1995 |

OTHER PUBLICATIONS

R. D. Rich, "Anaerobic Adhesives" in Handbook of Adhesive Technology, 29, 467-79, A. Pizzi and K. L. Mittal, eds., Marcel Dekker. Inc., New York (1994).

International Search Report issued in connection with International Patent Application No. PCT/US2010/032873 mailed on Jan. 28, 2011.

* cited by examiner

*Primary Examiner* — Robert D. Harlan
(74) *Attorney, Agent, or Firm* — Steven C. Bauman

(57) ABSTRACT

The present invention relates to cure accelerators useful for anaerobic curable compositions, such as adhesives and sealants.

10 Claims, 5 Drawing Sheets

CURE ACCELERATORS FOR ANAEROBIC CURABLE COMPOSITIONS

BACKGROUND OF THE INVENTION

1. Field of the Invention

The present invention relates to cure accelerators useful for anaerobic curable compositions, such as adhesives and sealants, which cure accelerators are within structure A

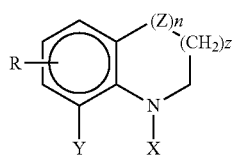

where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, or X and Y taken together form a carbocyclic ring having from 5-7 ring atoms; Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; R is optional but when present may occur up to 3 times on the aromatic ring and when present is $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; and n is 0 or 1; and z is 1-3, provided that when X is H, z is not 2 and is preferably 1.

2. Brief Description of Related Technology

Anaerobic adhesive compositions generally are well-known. See e.g. R. D. Rich, "Anaerobic Adhesives" in *Handbook of Adhesive Technology*, 29, 467-79, A. Pizzi and K. L. Mittal, eds., Marcel Dekker, Inc., New York (1994), and references cited therein. Their uses are legion and new applications continue to be developed.

Conventional anaerobic adhesives ordinarily include a free-radically polymerizable acrylate ester monomer, together with a peroxy initiator and an inhibitor component. Often, such anaerobic adhesive compositions also contain accelerator components to increase the speed with which the composition cures.

Desirable anaerobic cure-inducing compositions to induce and accelerate cure may include one or more of saccharin, toluidines, such as N,N-diethyl-p-toluidine ("DE-p-T") and N,N-dimethyl-o-toluidine ("DM-o-T"), acetyl phenylhydrazine ("APH"), maleic acid, and quinones, such as napthaquinone and anthraquinone. See e.g. U.S. Pat. Nos. 3,218,305 (Krieble), 4,180,640 (Melody), 4,287,330 (Rich) and 4,321,349 (Rich).

Saccharin and APH are used as standard cure accelerator components in anaerobic adhesive cure systems. The LOCTITE-brand anaerobic adhesive products currently available from Henkel. Corporation use either saccharin alone or both saccharin and APH in most of its anaerobic adhesives. These components however have come under regulatory scrutiny in certain parts of the world, and thus efforts have been undertaken to identify candidates as replacements.

Examples of other curatives for anaerobic adhesives include thiocaprolactam (e.g., U.S. Pat. No. 5,411,988) and thioureas [e.g., U.S. Pat. No. 3,970,505 (Hauser) (tetramethyl thiourea), German Patent Document Nos. DE 1 817 989 (alkyl thioureas and N,N'-dicyclohexyl thiourea) and 2 806 701 (ethylene thiourea), and Japanese Patent Document No. JP 07-308,757 (acyl, alkyl, alkylidene, alkylene and alkyl thioureas)], certain of the latter of which had been used commercially up until about twenty years ago.

Loctite (R&D) Ltd. discovered a new class of materials—trithiadiaza pentalenes—effective as curatives for anaerobic adhesive compositions. The addition of these materials into anaerobic adhesives as a replacement for conventional curatives (such as APH) surprisingly provides at least comparable cure speeds and physical properties for the reaction products formed therefrom. See U.S. Pat. No. 6,583,289 (McArdle).

U.S. Pat. No. 6,835,762 (Klemarczyk) provides an anaerobic curable composition based on a (meth)acrylate component with an anaerobic cure-inducing composition substantially free of acetyl phenylhydrazine and maleic acid and an anaerobic cure accelerator compound having the linkage —C(=O)—NH—NH— and an organic acid group on the same molecule, provided the anaerobic cure accelerator compound excludes 1-(2-carboxyacryloyl)-2-phenylhydrazine. The anaerobic cure accelerator is embraced by:

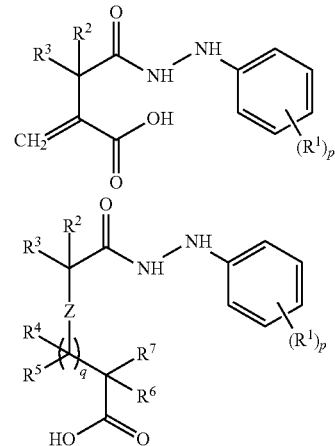

where $R^1$-$R^7$ are each independently selected from hydrogen and $C_{1-4}$; Z is a carbon-carbon single bond or carbon-carbon double bond; q is 0 or 1; and p is an integer between 1 and 5, examples of which are 3-carboxyacryloyl phenylhydrazine, methyl-3-carboxyacryloyl phenylhydrazine, 3-carboxypropanoyl phenylhydrazine, and methylene-3-carboxypropanoyl phenylhydrazine.

U.S. Pat. No. 6,897,277 (Klemarczyk) provides an anaerobic curable composition based on a (meth)acrylate component with an anaerobic cure-inducing composition substantially free of saccharin and an anaerobic cure accelerator compound within the following structure

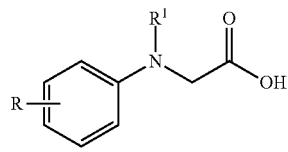

where R is selected from hydrogen, halogen, alkyl, alkenyl, hydroxyalkyl, hydroxyalkenyl, carboxyl, and sulfonato, and $R^1$ is selected from hydrogen, alkyl, alkenyl, hydroxyalkyl, hydroxyalkenyl, and alkaryl, an example of which is phenyl glycine and N-methyl phenyl glycine.

U.S. Pat. No. 6,958,368 (Messana) provides an anaerobic curable composition. This composition is based on a (meth) acrylate component with an anaerobic cure-inducing composition substantially free of saccharin and within the following structure

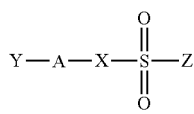

where Y is an aromatic ring, optionally substituted at up to five positions by $C_{1-6}$ alkyl or alkoxy, or halo groups; A is C=O, S=O or O=S=O; X is NH, O or S and Z is an aromatic ring, optionally substituted at up to five positions by $C_{1-6}$ alkyl or alkoxy, or halo groups, or Y and Z taken together may join to the same aromatic ring or aromatic ring system, provided that when X is NH, o-benzoic sulfimide is excluded from the structure. Examples of the anaerobic cure accelerator compound embraced by the structure above include 2-sulfobenzoic acid cyclic anhydride, and 3H-1,2-benzodithiol-3-one-1,1-dioxide.

Three Bond Co. Ltd., Tokyo, Japan has in the past described as a component in anaerobic adhesive and sealant compositions a component called tetrahydroquinoline ("THQ").

Notwithstanding the state of the art, there is an on-going desire to find alternative technologies for anaerobic cure accelerators to differentiate existing products and provide supply assurances in the event of shortages or cessation of supply of raw materials. Moreover, since certain of the raw materials used in conventional anaerobic cure inducing compositions have to one degree or another come under regulatory scrutiny, alternative components for anaerobic cure inducing compositions would be desirable. Accordingly, it would be desirable to identify new materials that function as cure components in the cure of anaerobically curable compositions.

SUMMARY OF THE INVENTION

The present invention relates to cure accelerators useful for anaerobic curable compositions, such as adhesives and sealants, which cure accelerators are within structure A

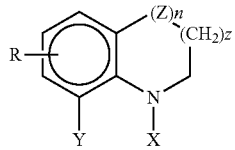

where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, or X and Y taken together form a carbocyclic ring having from 5-7 ring atoms; Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; R is optional but when present may occur up to 3 times on the aromatic ring and when present is $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; and n is 0 and 1; z is 1-3 and z is 1-3, provided that when X is H, z is not 2 and is preferably 1. More specifically, THQ-based or indoline-based adducts may be embraced by structure A as a cure accelerator.

For instance, adducts within structure A may be prepared as follows:

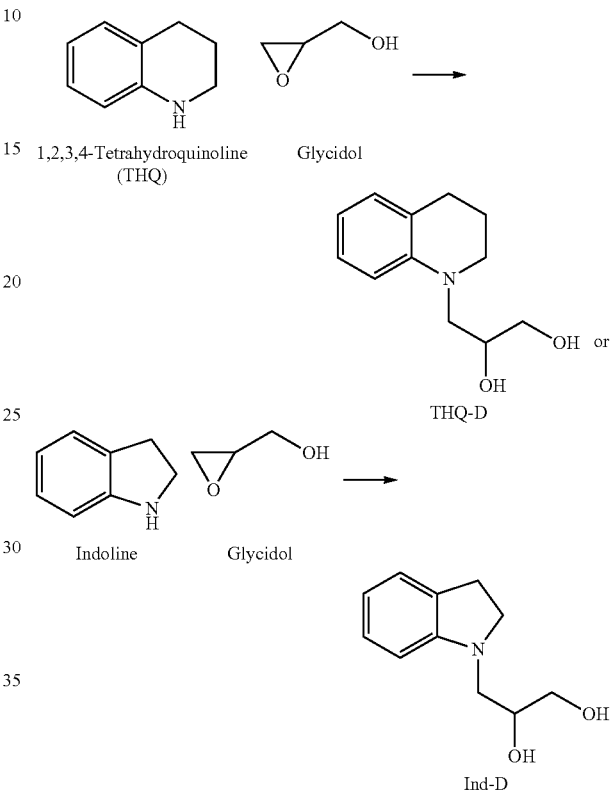

THQ-D and Ind-D are isomeric mixtures, represented as follows:

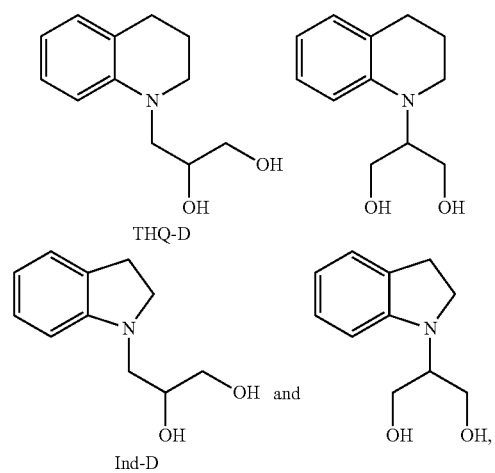

respectively.

Adducts within structure A may also be prepared with specific reference to N-alkylated adducts of THQ (or indoline, not shown) as follows:

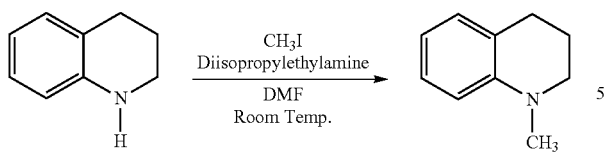

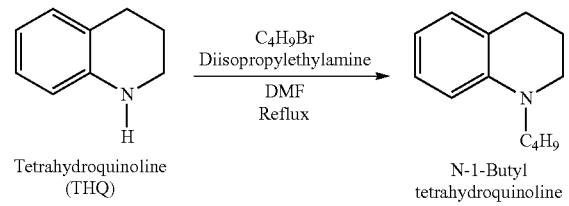

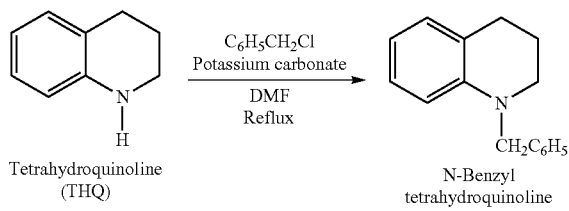

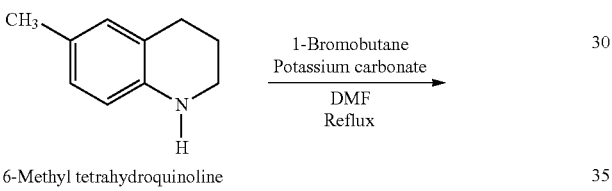

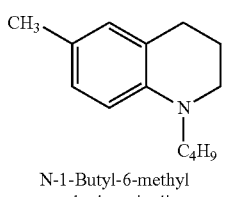

Thus, N-methyl-, N-butyl-, N-benzyl- and N-1-benzyl-6-methyl THQ (and N-methyl-, N-butyl, N-benzyl- and N-1-benzyl-6-methyl-indoline) adducts may be so prepared, and are also embraced by structure A.

The cure accelerator embraced by structure A may be prepared from reactants comprising: (a) at least one compound selected from compounds represented by structure I:

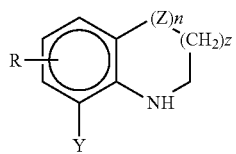

where R, Y, Z, n and z are as defined above, such as

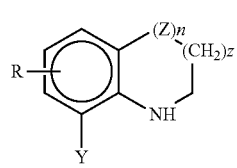

where R and z are as defined above, and (b) at least one compound selected from compounds represented by structure II:

$$(R^6)_n \overset{Z''}{\diagdown} (CH_2)_q$$

where Z'' is selected from —O—, —S—, or —NH—; q is 1-2; $R^6$ is independently selected from hydroxyalkyl, aminoalkyl, or thioalkyl; and n is at least 1, where the reaction product comprises at least two pendant functional groups independently selected from —OH, —NH$_2$ or —SH.

The present invention relates to cure accelerators useful for anaerobic curable compositions, such as adhesives and sealants, which cure accelerators are within structure A $$\underset{Y}{\overset{R}{\diagdown}}\underset{X}{\overset{(Z)_n}{\diagdown}}(CH_2)_z$$

where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, or X and Y taken together form a carbocyclic ring having from 5-7 ring atoms; Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; R is optional but when present may occur up to 3 times on the aromatic ring and when present is $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; and n is 0 and 1; and z is 1-3, provided that when X is H, z is not 2 and is preferably 1.

The anaerobic cure accelerator embraced by structure A may also be a reaction product prepared from reactants comprising (a) at least one compound selected from compounds represented by structure I:

where R, Y, Z, n and z are as defined above, such as

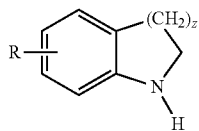

where R and z are as defined above, and (b) a reactant selected from an alkylating agent, an alkenylating agent or an alkarylating agent. For instance, such alkylating agents, alkenylating agents or alkarylating agents may be alkyl-, alkenyl- or alkaryl-halide compounds, such as an organic base like a tertiary amine or an inorganic base like potassium carbonate. Such alkyl-, alkenyl- or alkaryl-halide compounds include methyl, ethyl, propyl, propenyl, butyl, butenyl and benzyl halides, such as chloride, bromide and iodide. Other such alkylating agents, alkenylating agents or alkarylating agents include tosylates, mesylates and triflates, for instance.

Anaerobically curable adhesive and sealant compositions prepared from the above reaction products also are provided.

Methods of making reaction products are provided which are prepared from reactants comprising reacting: (a) at least one compound selected from structure I:

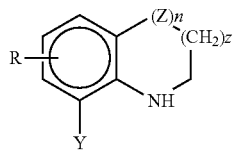

where R is optional, but when present may occur up to 4 times, with each instance being independent of the other. R is selected from halogen, $C_{1-20}$ alkyl, $C_{2-20}$ alkenyl, $C_{2-20}$ alkynyl, $C_{1-20}$ alkyloxy, $C_{2-20}$ alkenyloxy or $C_{2-20}$ alkynyloxy, Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH and z is 1-3; and (b) either: (i) at least one compound selected from structure II:

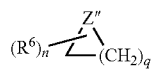

where Z" is selected from —O—, —S—, or —NH—; q is 1-2; $R^6$ is independently selected from hydroxyalkyl, aminoalkyl, or thioalkyl; and n is at least 1, where the reaction product of (a) and (b)(i) comprises at least two pendant functional groups independently selected from —OH, —NH$_2$ or —SH, or (ii) an alkylating agent, alkenylating agent or alkarylating agent.

DETAILED DESCRIPTION OF THE INVENTION

Figure 1:
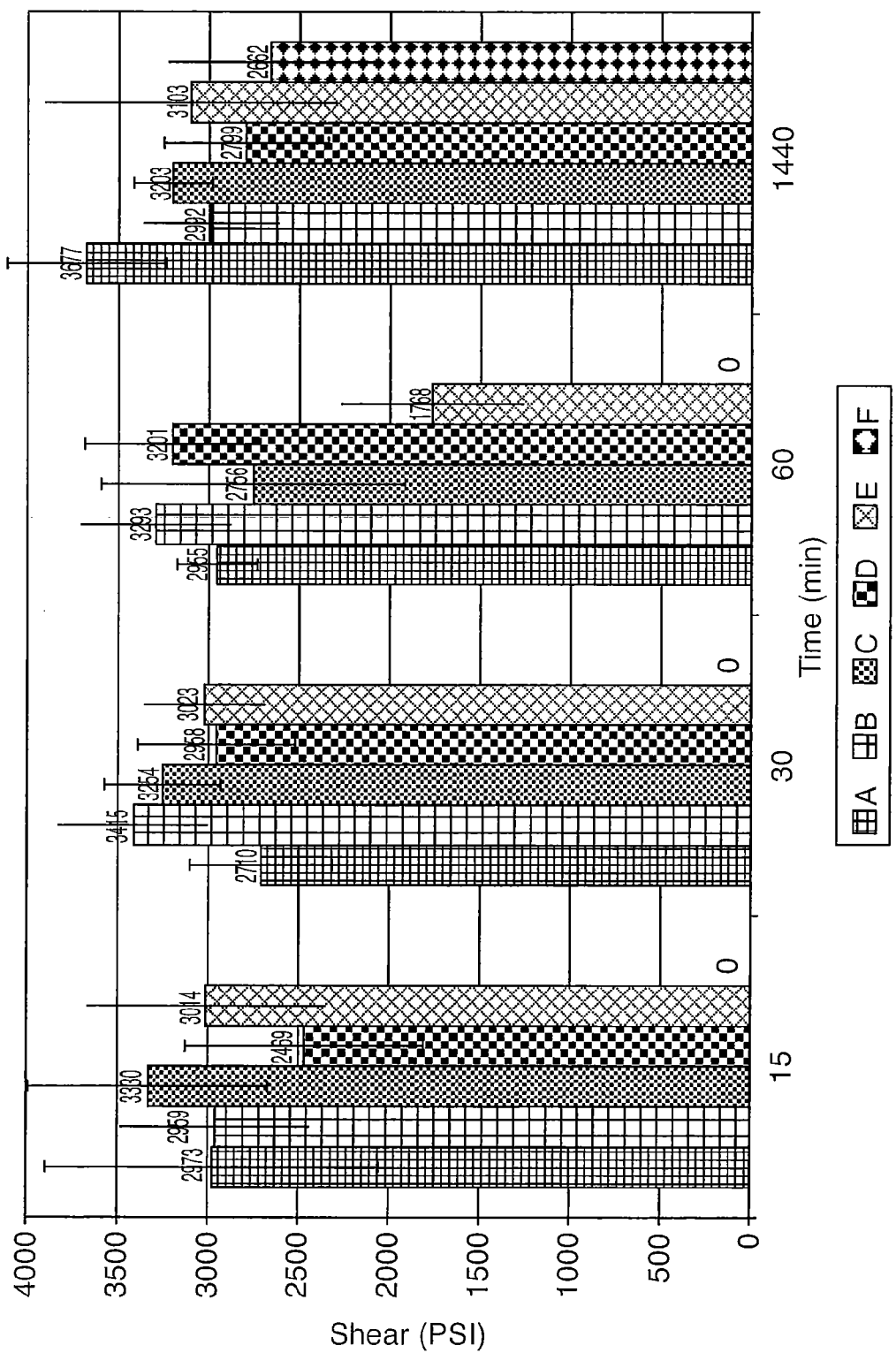
FIG. 1 depicts a plot of shear strength vs. time of anaerobic adhesive compositions, some of which using the inventive cure accelerators, on steel pin and collars.
Figure 2:
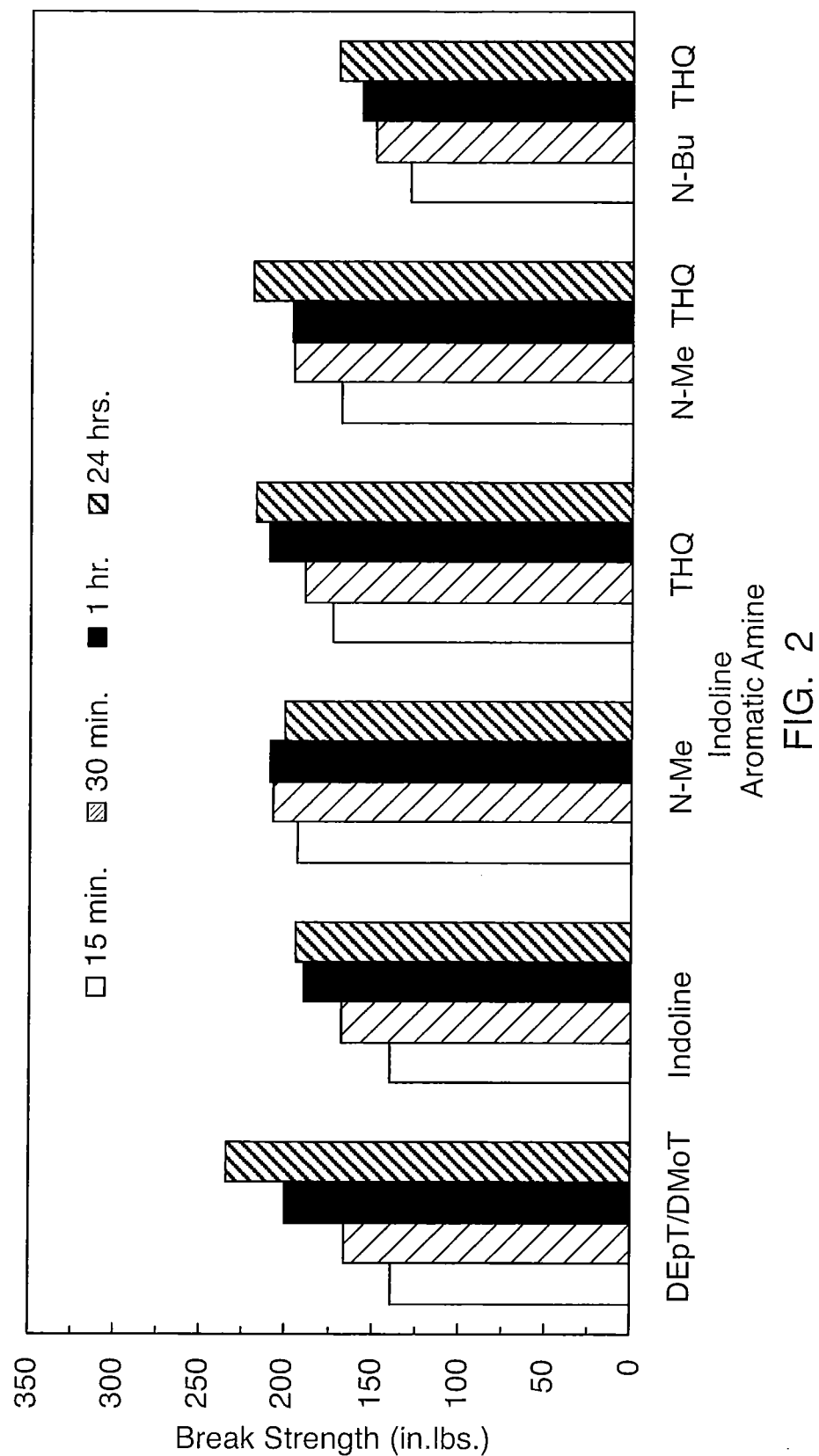
FIG. 2 depicts a plot of breakloose break strength vs. time of anaerobic adhesive compositions, some of which using the inventive cure accelerators, on steel nuts and bolts with a spacer therebetween.
Figure 3:
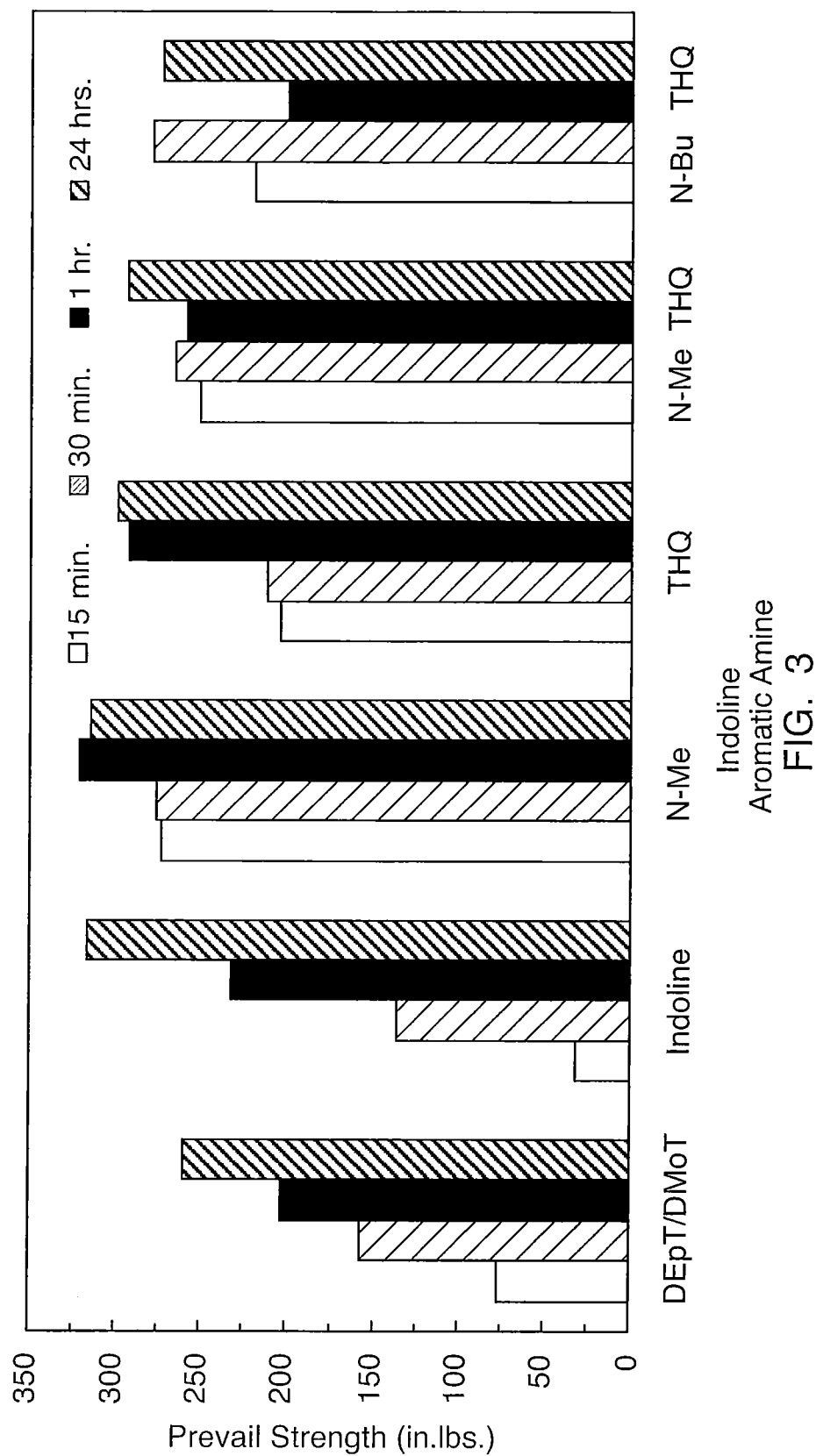
FIG. 3 depicts a plot of breakloose prevail strength vs. time of anaerobic adhesive compositions, some of which using the inventive cure accelerators, on steel nuts and bolts with a spacer therebetween.
Figure 4:
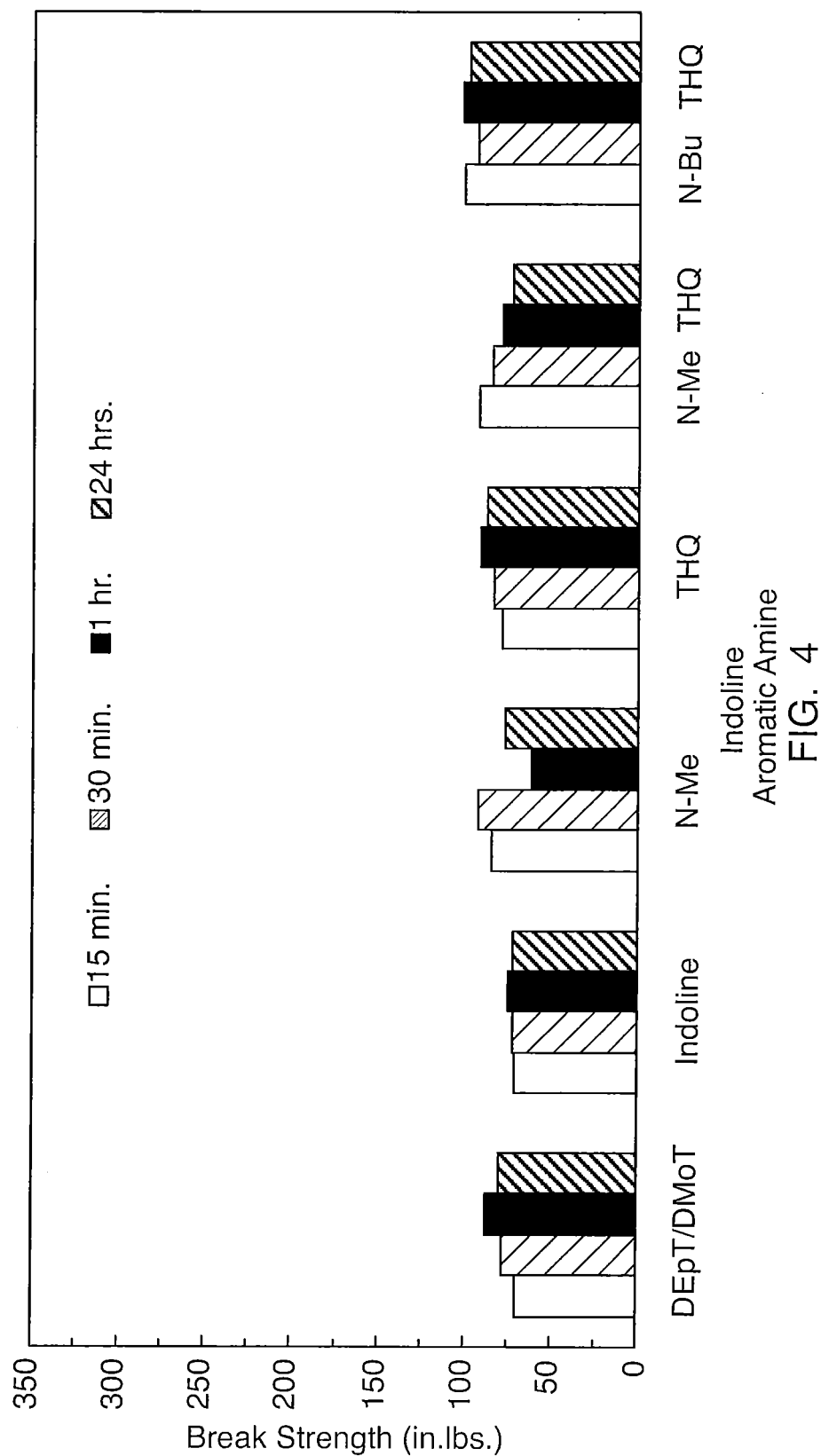
FIG. 4 depicts a plot of breakloose break strength vs. time of anaerobic adhesive compositions, some of which using the inventive cure accelerators, on stainless steel nuts and bolts with a spacer therebetween.
Figure 5:
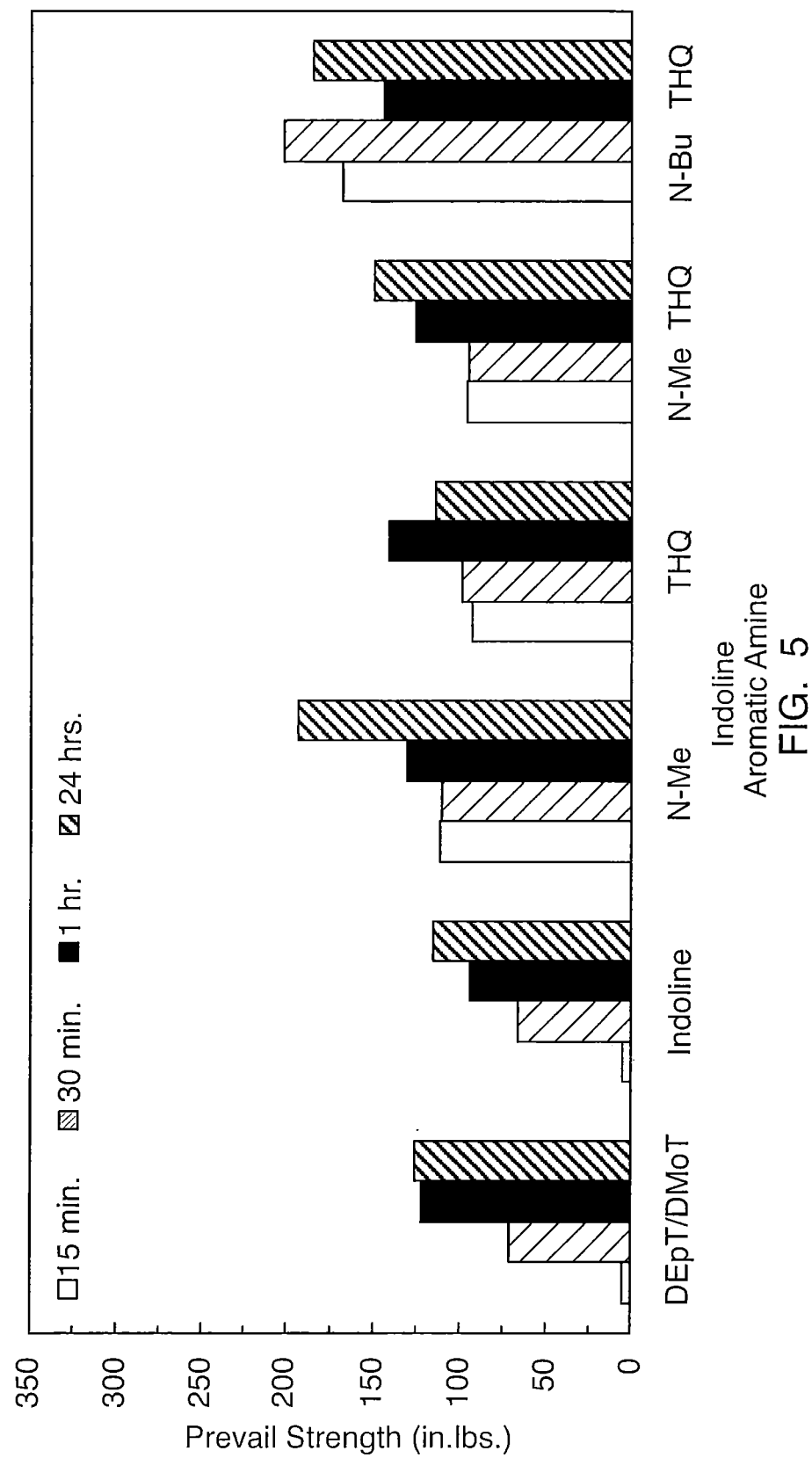
FIG. 5 depicts a plot of breakloose prevail strength vs. time of anaerobic adhesive compositions, some of which using the inventive cure accelerators, on stainless steel nuts and bolts with a spacer therebetween.

As noted above, the present invention provides anaerobic cure accelerators embraced by the following structure A

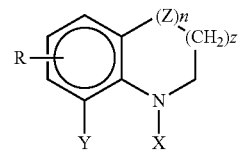

where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, or X and Y taken together form a carbocyclic ring having from 5-7 ring atoms; Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; R is optional but when present may occur up to 3 times on the aromatic ring and when present is $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; and n is 0 and 1; and z is 1-3, provided that when X is H, z is not 2 and is preferably 1.

For instance

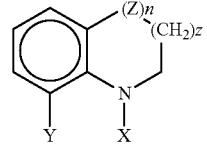

where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, or X and Y taken together form a carbocyclic ring having from 5-7 ring atoms; Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; and n is 0 or 1; and z is 1-3, provided that when X is H, z is not 2 and is preferably 1.

Or

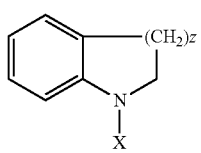

where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH and z is 1-3, provided that when X is H, z is not 2 and is preferably 1. More specifically, THQ-based or indoline-based components may be embraced by structure A as a cure accelerator.

As noted above, the present invention provides anaerobic cure accelerators embraced by the following structure A

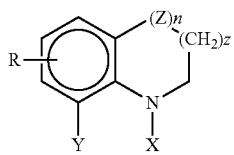

where X is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, or X and Y taken together form a carbocyclic ring having from 5-7 ring atoms; Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; R is optional but when present may occur up to 3 times on the aromatic ring and when present is $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH; and n is 0 and 1; and z is 1-3, provided that when X is H, z is not 2 and is preferably 1. More specifically, THQ-based or indoline-based components may be embraced by structure A as a cure accelerator.

For instance, adducts within structure A may be prepared as follows:

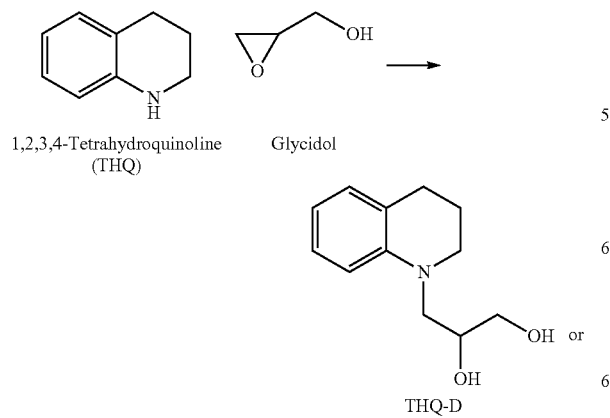

1,2,3,4-Tetrahydroquinoline (THQ)    Glycidol

THQ-D

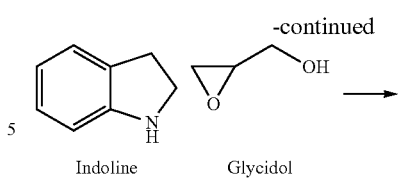

Indoline    Glycidol

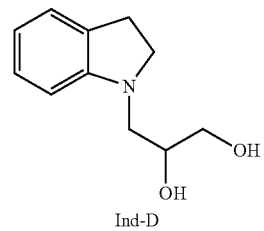

Ind-D

THQ-D and Ind-D are isomeric mixtures, represented as follows:

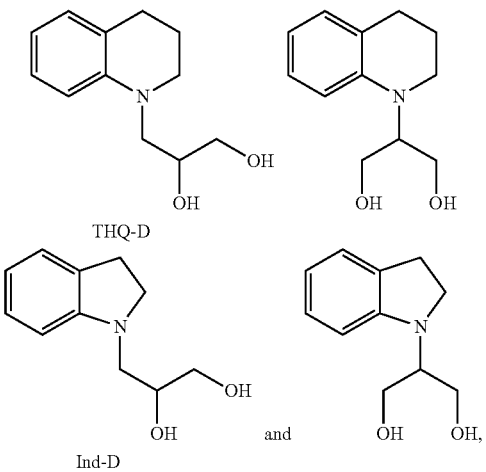

THQ-D

Ind-D    and respectively.

The anaerobic cure accelerator embraced by structure A

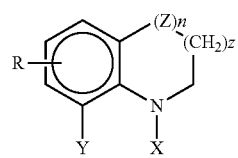

where R is optional, but when present may occur up to 3 times, with each instance being independent of the other. R is selected from halogen, $C_{1-20}$ alkyl, $C_{2-20}$ alkenyl, $C_{2-2}$ alkynyl, $C_{1-20}$ alkyloxy, $C_{2-20}$ alkenyloxy or $C_{2-20}$ alkynyloxy, X is selected from H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, and z is 1-3, may be a reaction product prepared from reactants comprising (a) at least one compound selected from compounds represented by structure I:

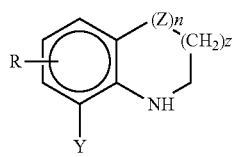

I where R is optional, but when present may occur up to 4 times, with each instance being independent of the other. R is selected from halogen, $C_{1-20}$ alkyl, $C_{2-20}$ alkenyl, $C_{2-20}$ alkynyl, $C_{1-20}$ alkyloxy, $C_{2-20}$ alkenyloxy or $C_{2-20}$ alkynyloxy, Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH and z is 1-3; and (b) at least one compound selected from compounds represented by structure II:

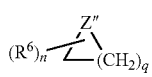

where Z" is selected from —O—, —S—, or —NH—; q is 1-2; $R^6$ is independently selected from hydroxyalkyl, aminoalkyl, or thioalkyl; and n is at least 1, where the reaction product comprises at least two pendant functional groups independently selected from —OH, —NH$_2$ or —SH.

The anaerobic cure accelerator embraced by structure A may be a reaction product prepared from reactants comprising (a) at least one compound selected from compounds represented by structure I:

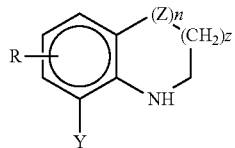

I where R is optional, but when present may occur up to 4 times, with each instance being independent of the other. R is selected from halogen, $C_{1-20}$ alkyl, $C_{2-20}$ alkenyl, $C_{2-20}$ alkynyl, $C_{1-20}$ alkyloxy, $C_{2-20}$ alkenyloxy or $C_{2-20}$ alkynyloxy, X is selected from H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH, Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —NH$_2$ or —SH and z is 1-3; and (b) an alkylating agent, alkenylating agent or alkarylating agent, in the presence of a base, such as noted above. Such alkylating agent, alkenylating agent or alkarylating agents may be exemplified by alkyl-, alkenyl- or alkaryl-halide compounds including methyl, ethyl, propyl, propenyl, butyl, butenyl and benzyl halides, such as chloride, bromide and iodide.

In addition, structure I and consequently structure A may include a saturated ring or an unsaturated ring, fused to the aromatic ring. An example of a compound embraced by structure A with an unsaturated ring is N-alkyl indole, such as N-methyl indole as shown below.

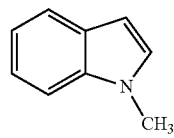

Also, compounds within structure A or I as appropriate, may include

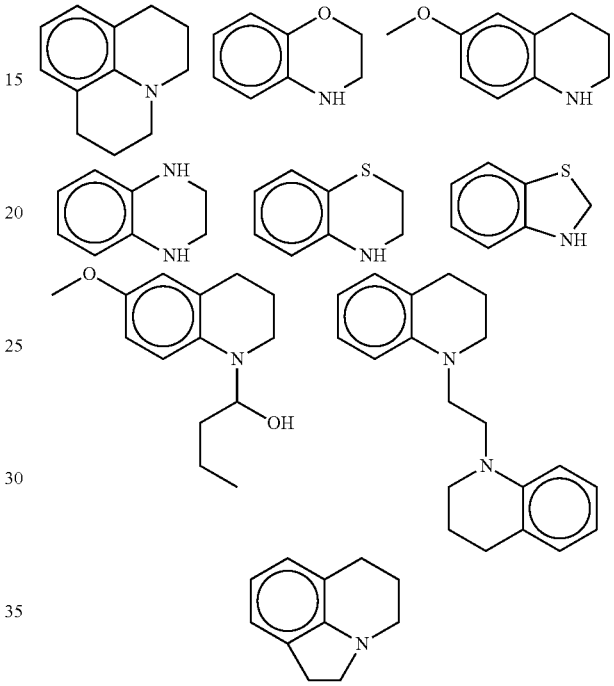

In the compounds of structure II above, Z" is desirably selected from —O—, —S—, or —NH—; q may be 1 to 4; $R^6$ may be independently selected from hydroxyalkyl, aminoalkyl, or thioalkyl; and n is at least 1. Desirably, the reactant represented by structure II is glycidol, as shown below:

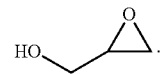

As discussed above, the reaction product comprises at least two pendant functional groups independently selected from —OH, —NH$_2$ or —SH. The reaction product comprises two or three pendant functional groups, such as hydroxy functional groups.

Desirably, the compound of structure I is either indoline itself or based on THQ, indoline or indole. Thus, the compound of structure A when based on THQ, indoline or indole is an alkyl, alkenyl, alkaryl, or functionalized alkyl, functionalized alkenyl or functionalized alkaryl adduct of THQ, indoline or indole.

The addition of such reaction products as cure accelerators into anaerobic adhesives as a replacement for some or all of the amount of conventional anaerobic cure accelerators (such as the toluidines, DE-p-T and DM-o-T, and/or APH) surprisingly provides at least comparable cure speeds and physical properties for the reaction products formed therefrom, as compared with those observed from conventional anaerobic curable compositions.

Methods of preparing the reaction product of compound(s) of structure I and compound(s) of structure II or the alkyl-, alkenyl- or alkaryl-halide compound to form compound(s) of structure A are provided. The methods involve reacting: (a) at least one compound selected from compounds represented by structure I:

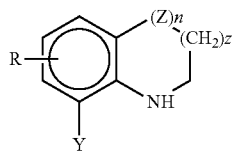

where R is optional, but when present may occur up to 4 times, with each instance being independent of the other. R is selected from halogen, $C_{1-20}$ alkyl, $C_{2-20}$ alkenyl, $C_{2-20}$ alkynyl, $C_{1-20}$ alkyloxy, $C_{2-20}$ alkenyloxy or $C_{2-20}$ alkynyloxy, Z is O, S, or NX', where X' is H, $C_{1-20}$ alkyl, $C_{2-20}$ alkenyl, or $C_{7-20}$ alkaryl, any of the latter three of which may be interrupted by one or more hereto atoms or functionalized by one or more groups selected from —OH, —$NH_2$ or —SH and z is 1-3; and (b) either:

(i) at least one compound selected from compounds represented by structure II:

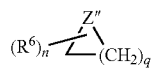

where Z" is selected from —O—, —S—, or —NH—; q is 1-2; $R^6$ is independently selected from hydroxyalkyl, aminoalkyl, or thioalkyl; and n is at least 1, where the reaction product comprises at least two pendant functional groups independently selected from —OH, —$NH_2$ or —SH, or (ii) in the presence of a base, an alkylating agent, alkenylating agent or alkarylating agent.

In preparing compounds of structure A, the reaction may be conducted in the presence of a solvent, in which case the compound of structure I may be dissolved in solvent prior to reaction with the compound of structure II or the alkylating agent, alkenylating agent or alkarylating agent, or vice versa.

The temperature employed in the reaction may also vary over a wide range. Where the components are combined in approximately chemical equivalent amounts or with one in slight excess, useful temperatures may vary from room temperature or below, e.g., 10° C. to 15° C., up to and including temperatures of 100° C. to 175° C. Reactions conducted at about 90° C. to 150° C. proceed smoothly.

The so formed reaction product(s) may be purified to remove impurities, such as reaction by-products or impurities that accompany the reactants. The reaction product(s) can be purified for example by distillation, filtration, stripping or chromatography, such that the purified reaction product(s) are essentially free of impurities, or comprise less than about 1 weight percent of impurities, or are free of impurities.

Anaerobic curable adhesive and sealant compositions generally are based on a (meth)acrylate component, together with an anaerobic cure-inducing composition. In the present invention, the anaerobic cure-inducing composition, has at least reduced levels of APH or toluidines (such as about 50% or less by weight of that which is used in conventional anaerobic curable compositions), is substantially free of APH or toluidines (less than about 10 weight percent, such as less than about 5 weight percent, and desirably less than about 1 weight percent) or is free of APH or toluidines. In place of some or all of APH or toluidines is the inventive cure accelerator—this is, compounds embraced by structure A.

(Meth)acrylate monomers suitable for use as the (meth)acrylate component in the present invention may be selected from a wide variety of materials, such as those represented by $H_2C=CGCO_2R^8$, where G may be hydrogen, halogen or alkyl groups having from 1 to about 4 carbon atoms, and $R^8$ may be selected from alkyl, cycloalkyl, alkenyl, cycloalkenyl, alkaryl, alkaryl or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone and the like.

Additional (meth)acrylate monomers suitable for use herein include polyfunctional (meth)acrylate monomers, for example di- or tri-functional (meth)acrylates such as polyethylene glycol di(meth)acrylates, tetrahydrofuran (meth)acrylates and di(meth)acrylates, hydroxypropyl (meth)acrylate ("HPMA"), hexanediol di(meth)acrylate, trimethylol propane tri(meth)acrylates ("TMPTMA"), diethylene glycol dimethacrylate, triethylene glycol dimethacrylates ("TRIEGMA"), tetraethylene glycol di(meth)acrylates, dipropylene glycol di(meth)acrylates, di-(pentamethylene glycol) di(meth)acrylates, tetraethylene diglycol di(meth)acrylates, diglycerol tetra(meth)acrylates, tetramethylene di(meth)acrylates, ethylene di(meth)acrylates, neopentyl glycol di(meth)acrylates, and bisphenol-A mono and di(meth)acrylates, such as ethoxylated bisphenol-A (meth)acrylate ("EBIPMA"), and bisphenol-F mono and di(meth)acrylates, such as ethoxylated bisphenol-A (meth)acrylate.

Still other (meth)acrylate monomers that may be used herein include silicone (meth)acrylate moieties ("SiMA"), such as those taught by and claimed in U.S. Pat. No. 5,605,999 (Chu), incorporated herein by reference.

Other suitable monomers include polyacrylate esters represented by the formula

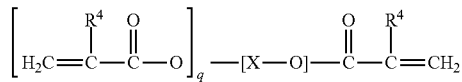

where $R^4$ is a radical selected from hydrogen, halogen or alkyl of from 1 to about 4 carbon atoms; q is an integer equal to at least 1, and preferably equal to from 1 to about 4; and X is an organic radical containing at least two carbon atoms and having a total bonding capacity of q plus 1. With regard to the upper limit for the number of carbon atoms in X, workable monomers exist at essentially any value. As a practical matter, however, a general upper limit is about 50 carbon atoms, such as desirably 30, and desirably about 20.

For example, X can be an organic radical of the formula:

where each of $Y^1$ and $Y^2$ is an organic radical, such as a hydrocarbon group, containing at least 2 carbon atoms, and desirably from 2 to about 10 carbon atoms, and Z is an organic radical, preferably a hydrocarbon group, containing at least 1 carbon atom, and preferably from 2 to about 10 carbon atoms.

Other classes of useful monomers are the reaction products of di- or tri-alkylolamines (e.g., ethanolamines or propanolamines) with acrylic acids, such as are disclosed in French Pat. No. 1,581,361.

Examples of useful acrylic ester oligomers include those having the following general formula:

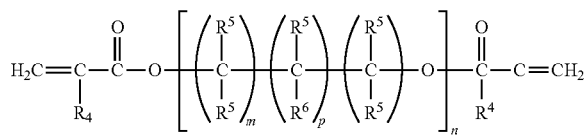

where $R^5$ represents a radical selected from hydrogen, lower alkyl of from 1 to about 4 carbon atoms, hydroxy alkyl of from 1 to about 4 carbon atoms, or

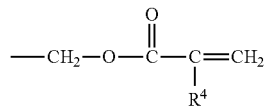

where $R^4$ is a radical selected from hydrogen, halogen, or lower alkyl of from 1 to about 4 carbon atoms; $R^6$ is a radical selected from hydrogen, hydroxyl, or

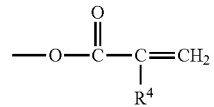

m is an integer equal to at least 1, e.g., from 1 to about 15 or higher, and desirably from 1 to about 8; n is an integer equal to at least 1, e.g., 1 to about 40 or more, and desirably between about 2 and about 10; and p is 0 or 1.

Typical examples of acrylic ester oligomers corresponding to the above general formula include di-, tri- and tetraethyleneglycol dimethacrylate; di(pentamethyleneglycol) dimethacrylate; tetraethyleneglycol diacrylate; tetraethyleneglycol di(chloroacrylate); diglycerol diacrylate; diglycerol tetramethacrylate; butyleneglycol dimethacrylate; neopentylglycol diacrylate; and trimethylolpropane triacrylate.

While di- and other polyacrylate esters, and particularly the polyacrylate esters described in the preceding paragraphs, can be desirable, monofunctional acrylate esters (esters containing one acrylate group) also may be used. When dealing with monofunctional acrylate esters, it is highly preferable to use an ester which has a relatively polar alcoholic moiety. Such materials are less volatile than low molecular weight alkyl esters and, more important, the polar group tends to provide intermolecular attraction during and after cure, thus producing more desirable cure properties, as well as a more durable sealant or adhesive. Most preferably, the polar group is selected from labile hydrogen, heterocyclic ring, hydroxy, amino, cyano, and halo polar groups. Typical examples of compounds within this category are cyclohexylmethacrylate, tetrahydrofurfuryl methacrylate, hydroxyethyl acrylate, hydroxypropyl methacrylate, t-butylaminoethyl methacrylate, cyanoethylacrylate, and chloroethyl methacrylate.

Another useful class of monomers is prepared by the reaction of a monofunctionally substituted alkyl or aryl acrylate ester containing an active hydrogen atom on the functional substituent. This monofunctional, acrylate-terminated material is reacted with an organic polyisocyanate in suitable proportions so as to convert all of the isocyanate groups to urethane or ureido groups. The monofunctional alkyl and aryl acrylate esters are preferably the acrylates and methacrylates containing hydroxy or amino functional groups on the nonacrylate portion thereof. Acrylate esters suitable for use have the formula

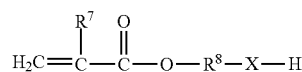

where X is selected from —O— and

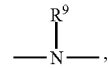

where $R^9$ is selected from hydrogen or lower alkyl of 1 through 7 carbon atoms; $R^7$ is selected from hydrogen, halogen (such as chlorine) or alkyl (such as methyl and ethyl radicals); and $R^8$ is a divalent organic radical selected from lower alkylene of 1 through 8 carbon atoms, phenylene and naphthylene. These groups upon proper reaction with a polyisocyanate, yield a monomer of the following general formula:

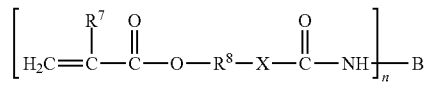

where n is an integer from 2 to about 6; B is a polyvalent organic radical selected from alkyl, alkenyl, cycloalkyl, cycloalkenyl, aryl, alkaryl, alkaryl and heterocyclic radicals both substituted and unsubstituted; and $R^7$, $R^8$ and X have the meanings given above.

The proportions in which the reactants may be combined can be varied somewhat; however, it is generally preferred to employ the reactants in chemically equivalent amounts up to a slight excess.

Of course, combinations of these (meth)acrylate monomers may also be used.

The (meth)acrylate component can comprise from about 10 to about 90 percent by weight of the composition, such as about 60 to about 90 percent by weight, based on the total weight of the composition.

Additional components have in the past been included in traditional anaerobic adhesives to alter the physical properties of either the formulation or the reaction products thereof. For instance, one or more of maleimide components, thermal resistance-conferring co reactants, diluent components reactive at elevated temperature conditions, mono- or poly-hydroxyalkanes, polymeric plasticizers, and chelators (see U.S. Pat. No. 6,391,993, incorporated herein by reference) may be included to modify the physical property and/or cure profile of the formulation and/or the strength or temperature resistance of the cured adhesive.

When used, the maleimide, co-reactant, reactive diluent, plasticizer, and/or mono- or poly-hydroxyalkanes may be present in an amount within the range of about 1 percent to about 30 percent by weight, based on the total weight of the composition.

The inventive compositions may also include other conventional components, such as free radical initiators, free radical co-accelerators, and inhibitors of free radical generation, as well as metal catalysts.

A number of well-known initiators of free radical polymerization are typically incorporated into anaerobic curable compositions including, without limitation, hydroperoxides, such as cumene hydroperoxide ("CHP"), para-menthane hydroperoxide, t-butyl hydroperoxide ("TBH") and t-butyl perbenzoate. Other peroxides include benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane, t-amyl hydroperoxide, 1,2,3,4-tetramethylbutyl hydroperoxide and combinations thereof.

Such peroxides are typically employed in the present invention in the range of from about 0.1 to about 10 percent by weight, based on the total weight of the composition, with about 1 to about 5 percent by weight being desirable.

As noted, conventional accelerators of free radical polymerization may also be used in conjunction with the inventive anaerobic cure accelerators, though in amounts less than that used in the past. Such accelerators are typically of the hydrazine variety (e.g., APH), as disclosed in U.S. Pat. Nos. 4,287,350 (Rich) and 4,321,349 (Rich). Maleic acid is usually added to APH-containing anaerobic cure inducing composition.

Co-accelerators of free radical polymerization may also be used in the compositions of the present invention including, without limitation, organic amides and imides, such as benzoic sulfimide (also known as saccharin) (see U.S. Pat. No. 4,324,349).

Stabilizers and inhibitors (such as phenols including hydroquinone and quinones) may also be employed to control and prevent premature peroxide decomposition and polymerization of the composition of the present invention, as well as chelating agents [such as the tetrasodium salt of ethylenediamine tetraacetic acid ("EDTA")] to trap trace amounts of metal contaminants therefrom. When used, chelating agents may ordinarily be present in the compositions in an amount from about 0.001 percent by weight to about 0.1 percent by weight, based on the total weight of the composition.

The inventive anaerobic cure accelerators may be used in amounts of about 0.1 to about 5 percent by weight, such as about 1 to about 2 percent by weight, based on the total weight of the composition. When used in combination with conventional accelerators (though at lower levels than such conventional accelerators), the inventive accelerators should be used in amounts of 0.01 to 5 percent by weight, such as 0.02 to 2 percent by weight, based on the total weight of the composition.

Metal catalyst solutions or pre-mixes thereof are used in amounts of about 0.03 to about 0.1 percent by weight.

Other additives such as thickeners, non-reactive plasticizers, fillers, toughening agents (such as elastomers and rubbers) and other well-known additives may be incorporated therein where the art-skilled believes it would be desirable to do so.

The present invention also provides methods of preparing and using the inventive anaerobic adhesive and sealant compositions, as well as reaction products of the compositions.

The compositions of the present invention may be prepared using conventional methods which are well known to those persons of skill in the art. For instance, the components of the inventive anaerobic adhesive and sealant compositions may be mixed together in any convenient order consistent with the roles and functions the components are to perform in the compositions. Conventional mixing techniques using known apparatus may be employed.

The compositions of this invention may be applied to a variety of substrates to perform with the desired benefits and advantages described herein. For instance, appropriate substrates may be constructed from steel, brass, copper, aluminum, zinc, and other metals and alloys, ceramics and thermosets. An appropriate primer for anaerobic curable compositions may be applied to a surface of the chosen substrate to enhance cure rate. Or, the inventive anaerobic cure accelerators may be applied to the surface of a substrate as a primer. See e.g. U.S. Pat. No. 5,811,473 (Ramos).

In addition, the invention provides a method of preparing an anaerobic curable composition, a step of which includes mixing together a (meth)acrylate component, an anaerobic cure inducing composition, and a compound embraced by structure A.

The invention also provides a process for preparing a reaction product from the anaerobic curable composition of the present invention, the steps of which include applying the composition to a desired substrate surface and exposing the composition to an anaerobic environment for a time sufficient to cure the composition.

This invention also provides a method of using as a cure accelerator for anaerobic curable composition, compounds of structure A. That method involves providing an anaerobic curable composition comprising a (meth)acrylate component and an anaerobic cure-inducing composition; providing as a cure accelerator for the anaerobic curable composition a compound embraced by structure A; and exposing the anaerobic curable composition and the cure accelerator to conditions favorable to cure the composition.

And the present invention provides a method of using an anaerobic cure accelerator compound, including (I) mixing the anaerobic cure accelerator compound in an anaerobic curable composition or (II) applying onto a surface of a substrate the anaerobic cure accelerator compound and applying thereover an anaerobic curable composition. Of course, the present invention also provides a bond formed between mated substrates with the inventive composition.

In view of the above description of the present invention, it is clear that a wide range of practical opportunities are provided. The following examples are illustrative purposes only, and are not to be construed so as to limit in any way the teaching herein.

EXAMPLES

Synthesis of Compounds of Structure A

An investigation was performed to evaluate reaction product(s) of glycidol and indoline or THQ and certain alkylated indoline or THQ adducts as replacements for APH as a cure accelerator in anaerobic curable compositions, such as adhesives.

Indoline-glycidol adducts were prepared in accordance with the synthetic scheme depicted below:

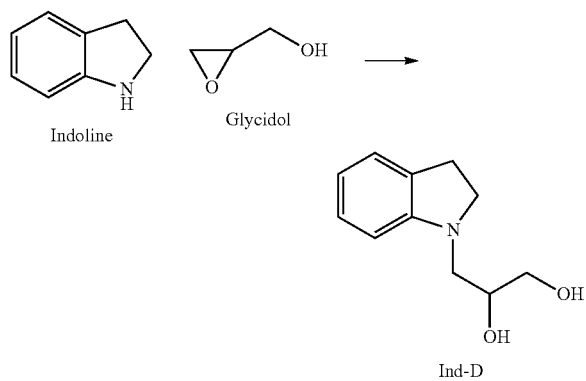

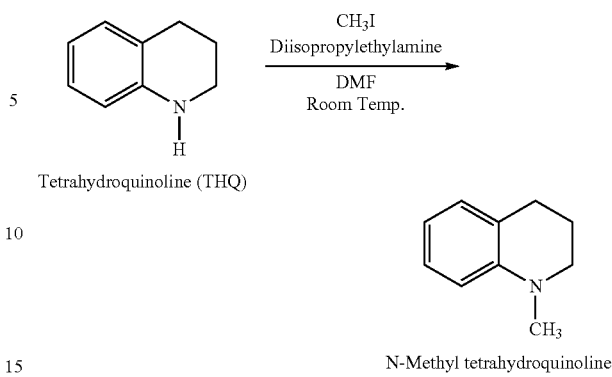

To a 500 ml four-neck round bottom flask, equipped with a condenser, addition funnel, nitrogen purge, magnetic stir bar and thermo-probe was added glycidol [62 grams; 805 moles]. The flask was placed in an ice bath, after which indoline [97 grams; 805 mmoles] was added with mixing and under a nitrogen purge. Mixing was continued for a period of time of 2 hours, at which point a solid was observed to form.

The so formed solid was recrystallized with acetone by heating the solid-acetone mixture to 50° C. with mixing until a solution forms. The temperature was then reduced to 38° C., where the solid was observed to reform. The mixture was then filtered, the solid collected and vacuum dried in an oven at 50° C.

THQ-glycidol adducts were prepared in accordance with the synthetic scheme depicted below:

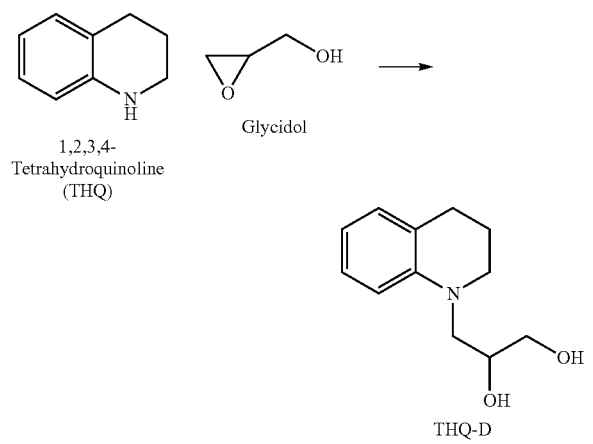

To a 500 ml four-neck round bottom flask, equipped with a condenser, addition funnel, nitrogen purge, magnetic stir bar and thermo-probe was added glycidol [8 grams; 108 mmoles] and THQ [14 grams; 108 mmoles]. The flask was placed on a hot plate maintained at 60° C. for 9 hours, during which time stirring continued. The reaction mixture was allowed to stand overnight at room temperature. 100 ml of deionized water was added, and the reaction mixture was again heated to 60° C.

The mixture was recrystallized with a combination of isopropyl alcohol/water, followed by deionized water, where a solid was observed to reform. The mixture was then filtered, the solid collected and vacuum dried in an oven at 50° C.

N-Methyl THQ was prepared in accordance with the synthetic scheme depicted below:

To a 1000 mL four-neck round bottom flask, equipped with a condenser, thermocouple, addition funnel, magnetic stir bar, and a nitrogen inlet, was added tetrahydroquinoline (53.2 g, 400 mmol), diisopropylethylamine (103.2 g, 800 mmol), and DMF (200 mL) with stirring. Methyl iodide (101.6 g, 800 mmol) is added dropwise from an addition funnel over 45 minutes, and the temperature is kept below 30° C. with a water/ice bath to control the exotherm. After the addition was complete, the reaction mixture was stirred overnight at ambient temperature, and the diisopropylethylammonium iodide salt precipitated from solution. The reaction mixture was added to 400 mL of $H_2O$ and 200 mL of $(i-Pr)_2O$ in a 1000 mL separatory funnel. The aqueous layer was separated and washed with 200 mL of $(i-Pr)_2O$. The two organic layers were combined and washed three times with 200 mL each of $H_2O$. The organic layer was separated, dried ($MgSO_4$), and filtered. Solvent was removed under reduced pressure. The residue was distilled under vacuum (ca. 1 Torr) over NaH (0.5 g). Yield=32.4 g (55%); B.P. (° C.)=85-88/0.7 Torr. $^1$H NMR ($CDCl_3$) δ 7.1 (t, 1, Ar—H), 6.9 (d, 1, Ar—H), 6.6 (t, 2, Ar—H), 3.2 (t, 2, N—$CH_2$), 2.8 (s, 3, N—$CH_3$), 2.7 (t, 2, Ar—$CH_2$), 1.9 (t, 2, $CH_2$); IR (neat) 2929, 2816, 1601, 1505, 1320, 1206, 1001, 741, 714.

N-1-Butyl THQ was prepared in accordance with the synthetic scheme depicted below:

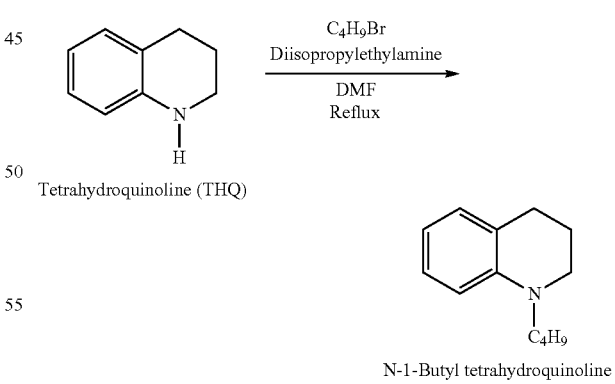

To a 1000 mL four-neck round bottom flask, equipped with a condenser, thermocouple, addition funnel, magnetic stir bar, and a nitrogen inlet, was added tetrahydroquinoline (53.2 g, 400 mmol), diisopropylethylamine (177.4 g, 600 mmol), 1-bromobutane (82.2 g, 600 mmol), and DMF (200 mL) with stirring. The solution was heated to reflux with stirring for two hours, and it was then cooled to ambient temperature. The diisopropylethylammonium bromide salt precipitated from solution on cooling. The reaction mixture was added to 400 mL of H₂O and 200 mL of (i-Pr)₂O in a 1000 mL separatory funnel. The aqueous layer was separated and washed with 200 mL of (i-Pr)₂O. The two organic layers were combined and washed three times with 200 mL each of H₂O. The organic layer was separated, dried (MgSO₄), and filtered. Solvent was removed under reduced pressure. The residue was distilled under vacuum (<1.0 Torr). Crude Yield=73.2 g (97%); B.P. (° C.)=108-110/0.6 Torr. ¹H NMR (CDCl₃) δ 7.0 (t, 1, Ar—H), 6.9 (d, 1, Ar—H), 6.6 (m, 2, Ar—H), 3.2 (m, 4, N—CH₂), 2.7 (t, 2, Ar—CH₂), 1.9 (m, 2, CH₂), 1.6 (m, 2, CH₂), 1.3 (m, 2, CH₂), 0.95 (t, 3, CH₃); IR (neat) 2929, 2860, 1601, 1503, 1344, 1193, 1104, 739, 715.

N-benzyl THQ was prepared in accordance with the synthetic scheme depicted below:

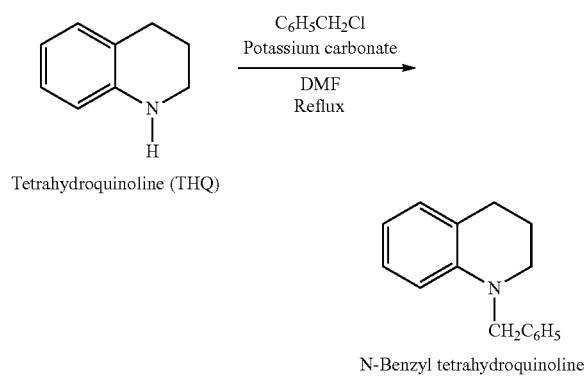

Tetrahydroquinoline (THQ)

N-Benzyl tetrahydroquinoline

To a 1000 mL four-neck round bottom flask, equipped with a condenser, thermocouple, addition funnel, magnetic stir bar, and a nitrogen inlet, was added THQ (26.2 g, 200 mmol), potassium carbonate (41.4 g, 300 mmol), benzyl chloride (37.8 g, 300 mmol), and DMF (100 mL) with stirring. The solution was heated to reflux with stirring for two hours, and it was then cooled to ambient temperature. The reaction mixture was added to 400 mL of H₂O and 200 mL of (i-Pr)₂O in a 1000 mL separatory funnel. The aqueous layer was separated and washed with 200 mL of (i-Pr)₂O. The two organic layers were combined and washed three times with 200 mL each of H₂O. The organic layer was separated, dried (MgSO₄), and filtered. Solvent was removed under reduced pressure. The residue was distilled under vacuum (<1.0 Torr). Crude Yield=46.4 g; B.P. (° C.)=155-157/1.0 Torr. ¹H NMR (CDCl₃) δ 7.3 (m, 5, Ar—H), 6.9 (m, 2, Ar—H), 6.6 (t, 1, Ar—H), 6.5 (d, 1, Ar—H), 4.4 (s, 2, Ar—N—CH₂), 3.3 (t, 2, N—CH₂), 2.8 (t, 2, Ar—CH₂), 2.0 (m, 2, CH₂); IR (neat) 2925, 2839, 1600, 1504, 1494, 1450, 1329, 1246, 1198, 1154, 969, 740, 730, 694.

N-1-butyl-6-methyl THQ was prepared in accordance with the synthetic scheme depicted below:

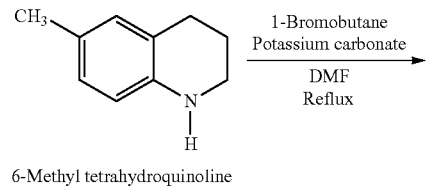

6-Methyl tetrahydroquinoline

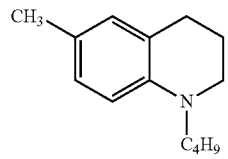

N-1-Butyl-6-methyl tetrahydroquinoline

To a 500 mL four-neck round bottom flask, equipped with a condenser, thermocouple, mechanical stirrer, and a nitrogen inlet, was added 6-methyl THQ (44.1 g, 300 mmol), potassium carbonate (62.1 g, 450 mmol), 1-bromobutane (61.7 g, 450 mmol), and N,N-dimethyl formamide (150 mL) with stirring. The solution was heated to reflux with stirring for a period of time of about 90 minutes, and it was then cooled to ambient temperature. The reaction mixture was added to 400 mL of H₂O and 200 mL of (i-Pr)₂O in a 1000 mL separatory funnel. The aqueous layer was separated and washed with 200 mL of (i-Pr)₂O. The two organic layers were combined and washed three times with 200 mL each of H₂O. The organic layer was separated, dried over anhydrous MgSO₄, and filtered. Solvent was removed under reduced pressure, and the crude product was distilled under vacuum (<1.0 Torr). Crude Yield=58.9 g (97%); B.P. (° C.)=114-115/0.8 Torr; ¹H NMR (CDCl₃) δ 6.8 (m, 2, Ar—H), 6.5 (d, 1, Ar—H), 3.2 (m, 4, N—CH₂), 2.7 (t, 2, Ar—CH₂), 2.1 (s, 3, CH₃), 1.9 (m, 2, CH₂), 1.55 (m, 2, CH₂), 1.35 (m, 2, CH₂), 0.95 (t, 3, CH₃).

Preparation of Anaerobic Curable Compositions

The following components listed in the table below were used to make anaerobic curable compositions for evaluation:

| Material | part |
| --- | --- |
| Monofunctional methacrylate | 15.08 |
| Difunctional methacrylate | 50.72 |
| Difunctional methacrylate resin | 23.15 |
| Acrylic acid | 6.06 |
| Stabilizer premix | 0.19 |
| Chelator premix | 0.96 |
| Saccharin | 0.96 |
| Accelerator | 0.96 |
| Initiator | 1.92 |
| | 100.00 |

Six formulations were thus prepared, five of which had an accelerator present (Samples A-E) and one of which did not (Sample F). In the table below, Samples A-F show whether an accelerator was present, and if so which one and whether it is within the scope of the present invention.

| A | APH |
| B | THQ |
| C | THQ_D |
| D | Indoline |
| E | Ind-D |
| F | No Accelerator |

In accordance with ASTM 4562, each of these formulations was applied to five replicates of steel pins and collars (having been degreased), and allowed to cure for periods of time, ranging from 15 minutes to 24 hours as noted in the table below. After these time periods, shear strength was measured and recorded. The measurements may be seen with reference to FIG. 1 and as depicted in the table below:

| Sample | Compressive Shear Strength (psi) at Specified Cure Times (Hrs.) | | | |
|---|---|---|---|---|
| | 0.25 | 0.5 | 1 | 24 |
| A | 2973 | 2710 | 2955 | 3677 |
| B | 2959 | 3415 | 3293 | 2992 |
| C | 3330 | 3254 | 2756 | 3203 |
| D | 2469 | 2958 | 3201 | 2799 |
| E | 3014 | 3023 | 1768 | 3103 |
| F | 0 | 0 | 0 | 2662 |

Next, six formulations were made to compare indoline (Sample No. 1), N-methyl indoline (Sample No. 2), THQ (Sample No. 3), N-methyl THQ (Sample No. 4), and N-1-butyl THQ (Sample No. 5) (referred to in FIGS. 2-5 on the x axis as an aromatic amine) and a control (Sample No. 1) that instead relies on a toluidine accelerator package. The constituents of the formulations may be seen with reference to the table below:

| Components | Sample No./Amt (phr) | | | | | |
|---|---|---|---|---|---|---|
| | 1 | 2 | 3 | 4 | 5 | 6 |
| PEGMA | 100 | 100 | 100 | 100 | 100 | 100 |
| Stabilizers | 1.19 | 1.19 | 1.19 | 1.19 | 1.19 | 1.19 |
| Saccharin | 1.73 | 1.73 | 1.73 | 1.73 | 1.73 | 1.73 |
| CHP | 1.00 | 1.00 | 1.00 | 1.00 | 1.00 | 1.00 |
| DE-p-T/ | 0.61/ | — | — | — | — | — |
| DM-o-T | 0.30 | | | | | |
| Indoline | — | 0.07 | — | — | — | — |
| N-Methyl Indoline | — | — | 0.08 | — | — | — |
| THQ | — | — | — | 0.08 | — | — |
| N-Methyl THQ | — | — | — | — | 0.09 | — |
| N-1-Butyl THQ | — | — | — | — | — | 0.11 |

Shelf Life Stability

The 82° C. stability of the formulations was determined according to an evaluation in which the formulation is judged to have acceptable shelf stability if the adhesive formulation remains liquid for 3 hours or longer at 82° C. Three specimens of each of the formulations containing either N-methyl THQ and N-methyl indoline were evaluated at 82° C., as were formulations containing the toluidine package and THQ and indoline themselves. Each formulation remained liquid for greater than 24 hours at this temperature.

Break-Prevail/Breakloose Strength

Break/prevail adhesion testing was performed according to ASTM D5649. Break torque is the initial torque required to decrease or eliminate the axial load in a seated assembly. Prevail/torque, after initial breakage of the bond, is measured at any point during 360° rotation of the nut. Prevail torque is normally determined at 180° rotation of the nut. Breakloose adhesion testing was preformed with a spacer between the nut and the seat of the bolt. Steel ⅜×16 nuts and bolts were degreased with 1,1,1-trichloroethylene, adhesive was applied to the bolt, and the nut was screwed onto the bolt with a steel collar as a spacer.

Twenty nut and bolt specimens of steel and stainless steel were assembled for each formulation tested. For the break/prevail adhesion tests, the specimens were maintained at ambient temperature for 15 minutes, 30 minutes, 1 hour, 4 hours and 24 hours after assembly (five specimens each). The break and prevail torque strengths (measured in in-lbs) were then recorded for five specimens of each formulation after 15 minutes, 30 minutes, 1 hour, 4 hours and 24 hours at ambient temperature (25° C.) and 45-50% relative humidity, respectively. The breakloose torque strengths (measured in in-lbs) were then recorded for five specimens of each formulation after 15 minutes, 30 minutes, 1 hour, and 24 hours at ambient temperature (25° C.) and 45-50% relative humidity, respectively. The torque strengths were measured using a calibrated automatic torque analyzer. The data for the evaluations on the steel nut and bolt assemblies is set forth below in the table and in FIGS. 2-3. The data for the evaluations on the stainless steel nut and bolt assemblies is set forth below in the table and in FIGS. 4-5.

| Physical Property | Sample No. | | | | | |
|---|---|---|---|---|---|---|
| | 1 | 2 | 3 | 4 | 5 | 6 |
| Break (in.lbs.) | Degreased Steel | | | | | |
| 15 min. | 139 | 140 | 194 | 174 | 169 | 129 |
| 30 min. | 166 | 168 | 208 | 190 | 197 | 150 |
| 60 min. | 200 | 190 | 210 | 211 | 198 | 157 |
| 24 hrs. | 235 | 195 | 201 | 219 | 221 | 171 |
| Prevail (in.lbs.) | | | | | | |
| 15 min. | 77 | 32 | 273 | 204 | 251 | 220 |
| 30 min. | 157 | 136 | 276 | 212 | 266 | 279 |
| 60 min. | 203 | 232 | 321 | 292 | 259 | 200 |
| 24 hrs. | 260 | 316 | 315 | 299 | 293 | 273 |
| Break (in.lbs.) | Degreased Stainless Steel | | | | | |
| 15 min. | 70 | 71 | 84 | 79 | 92 | 101 |
| 30 min. | 78 | 72 | 92 | 83 | 84 | 93 |
| 60 min. | 87 | 75 | 61 | 91 | 79 | 102 |
| 24 hrs. | 80 | 72 | 77 | 87 | 73 | 98 |
| Prevail (in.lbs.) | | | | | | |
| 15 min. | 5 | 5 | 111 | 93 | 96 | 168 |
| 30 min. | 71 | 66 | 110 | 99 | 95 | 202 |
| 60 min. | 122 | 94 | 130 | 141 | 126 | 144 |
| 24 hrs. | 126 | 115 | 194 | 114 | 150 | 185 |

This data indicates that formulations in accordance with this invention exhibited particularly good break and prevail properties at room temperature compared to traditional anaerobic adhesives when applied and cured on the steel substrates. The formulations in accordance with this invention exhibited particularly good breakloose properties at room temperature compared to traditional anaerobic adhesives when applied and cured on the steel substrates.

What is claimed is:

1. An anaerobic curable composition comprising
   (a) a (meth)acrylate component;
   (b) an anaerobic cure system; and
   (c) a reaction product prepared from reactants comprising:
      (a) at least one compound selected from the group of compounds represented by structure I:

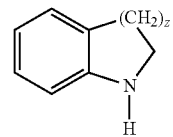

wherein z is 1-3; and
   (b) either:
      (i) at least one compound selected from the group of compounds represented by structure II:

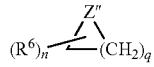

wherein Z" is selected from the group consisting of —O—, —S—, and —NH—; q is 1 to 4; $R^6$ is independently selected from the group consisting of hydroxyalkyl, aminoalkyl, and thioalkyl; and n is at least 1, wherein the reaction product comprises at least two pendant functional groups independently selected from the group consisting of —OH, —$NH_2$ and —SH; or (ii) an alkylating agent, alkenylating agent or alkarylating agent.

2. The composition according to claim 1, wherein the anaerobic curing system comprises a hydroperoxide selected from the group consisting of cumene hydroperoxide, para-menthane hydroperoxide, t-butyl hydroperoxide, t-butyl perbenzoate, benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane, t-amyl hydroperoxide, 1,2,3,4-tertramethylbutyl hydroperoxide and combinations thereof.

3. The composition according to claim 1, further comprising at least one accelerator.

4. The composition according to claim 3, wherein the accelerator is selected from the group consisting of amines, amine oxides, sulfonamides, metals and sources thereof, acids, and mixtures thereof.

5. The composition according to claim 3, wherein the accelerator is selected from the group consisting of triazines, ethanolamine, diethanolamine, triethanolamine, N,N-dimethyl aniline, benzene sulphonimide, cyclohexyl amine, triethyl amine, butyl amine, saccharin, N,N-diethyl-p-toluidine, N,N-dimethyl-o-toluidine, acetyl phenylhydrazine, maleic acid, and mixtures thereof.

6. The composition according to claim 1, further comprising at least one stabilizer.

7. The composition according to claim 6, wherein the stabilizer is selected from the group consisting of benzoquinone, naphthoquinone, anthraquinone, hydroquinone, methoxyhydroquinone, butylated hydroxy toluene, ethylene diamine tetraacetic acid or a salt thereof, and mixtures thereof.

8. The composition according to claim 1, wherein in (a) the compound of structure I is THQ, indoline or indole.

9. The composition according to claim 1, wherein in (b) the compound of structure II is glycidol.

10. The composition according to claim 1, wherein (b) comprises an alkyl halide.

\* \* \* \* \*